United States Patent

(12) United States Patent
Coskun et al.

(10) Patent No.: US 11,541,123 B2
(45) Date of Patent: Jan. 3, 2023

(54) DUAL AMYLIN AND CALCITONIN RECEPTOR AGONISTS AND USES THEREOF

(71) Applicant: Eli Lilly and Company, Indianapolis, IN (US)

(72) Inventors: Tamer Coskun, Carmel, IN (US); Hongchang Qu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/554,022

(22) Filed: Dec. 17, 2021

(65) Prior Publication Data
US 2022/0193245 A1 Jun. 23, 2022

Related U.S. Application Data

(60) Provisional application No. 63/127,186, filed on Dec. 18, 2020.

(51) Int. Cl.
*A61K 47/62* (2017.01)
*A61K 47/54* (2017.01)
*A61P 3/04* (2006.01)
*A61K 38/22* (2006.01)
*A61P 3/10* (2006.01)

(52) U.S. Cl.
CPC .............. *A61K 47/62* (2017.08); *A61K 38/22* (2013.01); *A61K 47/54* (2017.08); *A61K 47/542* (2017.08); *A61K 47/545* (2017.08); *A61P 3/04* (2018.01); *A61P 3/10* (2018.01)

(58) Field of Classification Search
CPC ........ A61K 47/62; A61K 38/22; A61K 47/54; A61K 47/542; A61K 47/545; A61P 3/04; A61P 3/10
See application file for complete search history.

(56) References Cited

U.S. PATENT DOCUMENTS

| 4,639,510 A * | 1/1987 | Orlowski ............. C07K 14/585 530/307 |
| 11,084,861 B2 * | 8/2021 | Abraham .................. A61P 3/04 |
| 2020/0024322 A1 * | 1/2020 | Abraham .................. A61P 3/04 |
| 2021/0032299 A1 * | 2/2021 | Alsina-Fernandez ........................ C07K 14/4703 |

FOREIGN PATENT DOCUMENTS

| WO | 2010/085700 | 7/2010 |
| WO | 2015/071229 | 5/2015 |
| WO | 2016/034604 | 3/2016 |
| WO | 2020/039051 | 2/2020 |

OTHER PUBLICATIONS

International Search Report of the International Searching Authority pertaining to International Application No. PCT/US2021/063990; dated Apr. 4, 2022 6 pages.
Written Opinion of the International Searching Authority pertaining to International Application No. PCT/US2021/063990; dated Apr. 4, 2022; 6 pages.

* cited by examiner

*Primary Examiner* — Marcela M Cordero Garcia
(74) *Attorney, Agent, or Firm* — Megan Fuller

(57) ABSTRACT

The present disclosure related to the field of medicine. More particularly, the disclosure is in the field of treatment of diabetes, obesity, and/or dyslipidemia. The disclosure relates to compounds that agonize both the calcitonin and amylin receptors and can lower food intake, body weight, glucose and/or triglycerides, so can be used to treat diabetes, obesity and/or dyslipidemia. The present disclosure also includes pharmaceutical compositions containing such compounds and therapeutic uses of such compounds and compositions.

13 Claims, No Drawings

Specification includes a Sequence Listing.

SEQUENCE LISTING

```
<160> NUMBER OF SEQ ID NOS: 13

<210> SEQ ID NO 1
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: N-terminus is acetylated
<220> FEATURE:
<221> NAME/KEY: MISC_FEATURE
<222> LOCATION: (14)..(14)
<223> OTHER INFORMATION: Xaa at position 14 is Aib
<220> FEATURE:
<221> NAME/KEY: MOD_RES
<222> LOCATION: (32)..(32)
<223> OTHER INFORMATION: C-terminus is amidated

<400> SEQUENCE: 1

Ala Ser His Leu Ser Thr Ala Val Leu Gly Lys Leu Ser Xaa Glu Leu
1               5                   10                  15

His Lys Leu Glu Asp Tyr Pro Arg Thr Asp Val Gly Ala Glu Ser Pro
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: N-terminus is acetylated
<220> FEATURE:
<221> NAME/KEY: MOD_RES
<222> LOCATION: (11)..(11)
<223> OTHER INFORMATION: The Lys at position 11 is chemically modified
      by conjugation of the epsilon amino group of the Lys sidechain
      with
      2-[2-(2-Amino-ethoxy)-ethoxy]-acetyl2-(gamma-Glu)-CO-(CH2)18-CO2H
<220> FEATURE:
<221> NAME/KEY: MISC_FEATURE
<222> LOCATION: (14)..(14)
<223> OTHER INFORMATION: Xaa at position 14 is Aib
<220> FEATURE:
<221> NAME/KEY: MOD_RES
<222> LOCATION: (32)..(32)
<223> OTHER INFORMATION: C-terminus is amidated
```

```
<400> SEQUENCE: 2

Ala Ser His Leu Ser Thr Ala Val Leu Gly Lys Leu Ser Xaa Glu Leu
1               5                   10                  15

His Lys Leu Glu Asp Tyr Pro Arg Thr Asp Val Gly Ala Glu Ser Pro
            20                  25                  30

<210> SEQ ID NO 3
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(7)
<220> FEATURE:
<221> NAME/KEY: MOD_RES
<222> LOCATION: (37)..(37)
<223> OTHER INFORMATION: C-terminus is amidated

<400> SEQUENCE: 3

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Thr Asn Val
            20                  25                  30

Gly Ser Asn Thr Tyr
            35

<210> SEQ ID NO 4
<211> LENGTH: 32
<212> TYPE: PRT
<213> ORGANISM: Homo sapiens
<220> FEATURE:
<221> NAME/KEY: DISULFID
<222> LOCATION: (1)..(7)
<220> FEATURE:
<221> NAME/KEY: MOD_RES
<222> LOCATION: (32)..(32)
<223> OTHER INFORMATION: C-terminus is amidated

<400> SEQUENCE: 4

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 5
<211> LENGTH: 37
<212> TYPE: PRT
<213> ORGANISM: Homo sapiens
<220> FEATURE:
<221> NAME/KEY: DISULFID
<222> LOCATION: (2)..(7)
<220> FEATURE:
<221> NAME/KEY: MOD_RES
<222> LOCATION: (37)..(37)
<223> OTHER INFORMATION: C-terminus is amidated

<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
            35
```

```
<210> SEQ ID NO 6
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: The Lys at position 20 is chemically modified
      by conjugation of the epsilon amino group of the Lys sidechain
      with
      2-[2-(2-Amino-ethoxy)-ethoxy]-acetyl)2-(gamma-Glu)-CO-(CH2)16-CO2H

<400> SEQUENCE: 6

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 7
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: The Lys at position 20 is chemically modified
      by conjugation of the epsilon amino group of the Lys sidechain
      with
      2-[2-(2-Amino-ethoxy)-ethoxy]-acetyl)2-(gamma-Glu)-CO-(CH2)18-CO2H
<220> FEATURE:
<221> NAME/KEY: MOD_RES
<222> LOCATION: (34)..(34)
<223> OTHER INFORMATION: C-terminus is amidated

<400> SEQUENCE: 7

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 8
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: The Lys at position 17 is chemically modified
``` by conjugation of the epsilon amino group of the Lys sidechain
with
2-[2-(2-Amino-ethoxy)-ethoxy]-acetyl)-(gamma-Glu)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: C-terminus is amidated

<400> SEQUENCE: 8

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
            35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (20)..(20)
<223> OTHER INFORMATION: The Lys at position 20 is chemically modified
    by conjugation of the epsilon amino group of the Lys sidechain
    with
    2-[2-(2-Amino-ethoxy)-ethoxy]-acetyl)2-(gamma-Glu)2-CO-(CH2)18-CO2H
<220> FEATURE:
<221> NAME/KEY: MISC_FEATURE
<222> LOCATION: (22)..(22)
<223> OTHER INFORMATION: Xaa at position 22 is 1Nal
<220> FEATURE:
<221> NAME/KEY: MOD_RES
<222> LOCATION: (39)..(39)
<223> OTHER INFORMATION: C-terminus is amidated

<400> SEQUENCE: 9

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
            20                  25                  30

Ser Gly Ala Pro Pro Pro Ser
            35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE

```
<222> LOCATION: (13)..(13)
<223> OTHER INFORMATION: Xaa at position 13 is Aib
<220> FEATURE:
<221> NAME/KEY: MOD_RES
<222> LOCATION: (20)..(20)
<223> OTHER INFORMATION: The Lys at position 20 is chemically modified
      by conjugation of the epsilon amino group of the Lys sidechain
      with
      2-[2-(2-Amino-ethoxy)-ethoxy]-acetyl)2-(gamma-Glu)-CO-(CH2)18-CO2H
<220> FEATURE:
<221> NAME/KEY: MOD_RES
<222> LOCATION: (39)..(39)
<223> OTHER INFORMATION: C-terminus is amidated

<400> SEQUENCE: 10

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
                20                  25                  30

Ser Gly Ala Pro Pro Pro Ser
        35

<210> SEQ ID NO 11
<211> LENGTH: 44
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (44)..(44)
<223> OTHER INFORMATION: C-terminus is amidated

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Lys
        35                  40

<210> SEQ ID NO 12
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: The Lys at position 20 is chemically modified
      by conjugation of the epsilon amino group of the Lys sidechain
      with -(gamma-Glu)-CO-(CH2)14-CH3

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
                20                  25                  30

<210> SEQ ID NO 13
<211> LENGTH: 275
<212> TYPE: PRT
<213> ORGANISM: Artificial Sequence
<220> FEATURE:
<223> OTHER INFORMATION: Synthetic Construct

<400> SEQUENCE: 13
```

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

Gly Gly Gly Ser Gly Gly Gly Ser Gly Gly Gly Ser Ala Glu
        35              40              45

Ser Lys Tyr Gly Pro Pro Cys Pro Pro Cys Pro Ala Pro Glu Ala Ala
    50              55              60

Gly Gly Pro Ser Val Phe Leu Phe Pro Pro Lys Pro Lys Asp Thr Leu
65              70              75                  80

Met Ile Ser Arg Thr Pro Glu Val Thr Cys Val Val Val Asp Val Ser
            85              90                  95

Gln Glu Asp Pro Glu Val Gln Phe Asn Trp Tyr Val Asp Gly Val Glu
            100             105             110

Val His Asn Ala Lys Thr Lys Pro Arg Glu Glu Gln Phe Asn Ser Thr
        115             120             125

Tyr Arg Val Val Ser Val Leu Thr Val Leu His Gln Asp Trp Leu Asn
    130             135             140

Gly Lys Glu Tyr Lys Cys Lys Val Ser Asn Lys Gly Leu Pro Ser Ser
145             150             155             160

Ile Glu Lys Thr Ile Ser Lys Ala Lys Gly Gln Pro Arg Glu Pro Gln
            165             170             175

Val Tyr Thr Leu Pro Pro Ser Gln Glu Glu Met Thr Lys Asn Gln Val
            180             185             190

Ser Leu Thr Cys Leu Val Lys Gly Phe Tyr Pro Ser Asp Ile Ala Val
            195             200             205

Glu Trp Glu Ser Asn Gly Gln Pro Glu Asn Asn Tyr Lys Thr Thr Pro
    210             215             220

Pro Val Leu Asp Ser Asp Gly Ser Phe Phe Leu Tyr Ser Arg Leu Thr
225             230             235             240

Val Asp Lys Ser Arg Trp Gln Glu Gly Asn Val Phe Ser Cys Ser Val
            245             250             255

Met His Glu Ala Leu His Asn His Tyr Thr Gln Lys Ser Leu Ser Leu
            260             265             270

Ser Leu Gly
        275
```

DUAL AMYLIN AND CALCITONIN RECEPTOR AGONISTS AND USES THEREOF

The present disclosure relates to the field of medicine. More particularly, the disclosure is in the field of treatment of diabetes, obesity, non-alcoholic steatohepatitis (NASH), and/or dyslipidemia. The disclosure relates to compounds that agonize both the amylin and calcitonin receptors and can therefore lower food intake, body weight, glucose, and/or triglycerides, and may be used to treat diabetes, obesity, NASH, and/or dyslipidemia. The present disclosure also includes pharmaceutical compositions containing such compounds, and therapeutic uses of such compounds and pharmaceutical compositions.

Amylin is a peptide hormone that is co-secreted with insulin from the pancreatic β-cells and is deficient in people with diabetes. It inhibits glucagon secretion, delays gastric emptying, and acts as a satiety agent. An amylin analog, pramlintide, is available to treat diabetic patients who use insulin because it lowers blood sugar levels. The elimination half-life of this medicine is less than an hour and it is used at mealtimes, so a patient needs multiple doses in one day to use this medicine in therapy.

Calcitonin is a hormone that is produced in the thyroid gland that plays a role in regulating levels of calcium and phosphate in the blood. Salmon calcitonin is available to treat conditions with high levels of calcium in the blood, such as hypercalcemia. Salmon calcitonin has a short half-life of less than two hours, so a patient needs to dose once a day or multiple times a day to use this peptide in therapy.

It has been shown that compounds which agonize both the amylin and calcitonin receptors have positive effects such as lowering blood glucose levels and inducing weight loss. See WO2016/034604, WO2015/071229 and WO2010/085700. The natural half-life of known amylin and calcitonin receptor agonists is short, so an extended time action is desirable. However, chemical modifications intended to extend activity time have also, thus far, shown a decrease in potency. In addition, agonists of the amylin and calcitonin receptors have stability challenges due to their tendency to fibrillate and the presence of a labile disulfide bond at neutral pH.

There is a need for alternative compounds that agonize both the amylin and calcitonin receptors. In addition, the need exists for dual amylin and calcitonin receptor agonists with extended time action and preserved potency. Therapeutically desirable compounds would agonize both the amylin and calcitonin receptors and provide one or more advantageous properties such as lowering food intake, lowering body weight, lowering blood glucose levels, lowering triglycerides, and/or lowering insulin levels. In addition, therapeutically desirable compounds may have one or more additional advantageous properties such as extended time action with preserved or improved potency in agonizing both the amylin and calcitonin receptors, a low risk of immunogenic response, chemical stability at a neutral pH, and/or a low risk of fibrillation.

Further, combination of a dual amylin and calcitonin receptor agonist of the present disclosure, optionally combined with an incretin or incretin analog, is desired to provide treatment for diabetes, obesity, NASH, and/or dyslipidemia. Such combination will also preferably be more effective than either molecule alone. For example, such treatment with such combination may allow for use of lower doses of either or both molecules as compared to each molecule alone, potentially leading to lower side effects (or a shorter duration of one or the other therapy) while maintaining efficacy. It is believed that the novel combination(s) provided herein will be effective treatments for diabetes, obesity, NASH, and/or dyslipidemia.

Accordingly, the present disclosure provides a method of treating diabetes, obesity, NASH, and/or dyslipidemia, comprising administering to a patient in need of such treatment an effective amount of a dual amylin and calcitonin receptor agonist with an effective amount of an incretin or incretin analog. The present disclosure further provides a method of treating clinical or pre-clinical diabetes, obesity, NASH, and/or dyslipidemia comprising administering to a patient in need of such treatment an effective amount of a dual amylin and calcitonin receptor agonist in combination with an effective amount of incretin or incretin analog.

Certain presently disclosed compounds which agonize the amylin and calcitonin receptors show an effective reduction in food intake and body weight, as well as glucose and insulin lowering. Further, certain presently disclosed compounds show a decreased risk of immunogenicity and a low level of fibrillation. The pharmacokinetic properties of certain presently disclosed compounds show greatly extended half-life, which will enable dosing of once a week of these compounds for use in therapy. Other embodiments of the present disclosure are useful for making such compounds for use in therapy. Methods for combining the presently disclosed compounds with incretins or incretin analogs are also disclosed.

One of the compounds of the disclosure, Compound I, comprises the following sequence: Acetyl-ASHL-STAVLGKLS-Aib-ELHKLEDYPRTDVGAESP-NH$_2$ (SEQ ID NO:1), or a pharmaceutically acceptable salt thereof. Below is a depiction of the structure of Compound I using the standard single letter amino acid codes with the exception of residues Acetyl-A1, Aib14, and P32-NH$_2$, where the structures of these amino acid residues have been expanded:

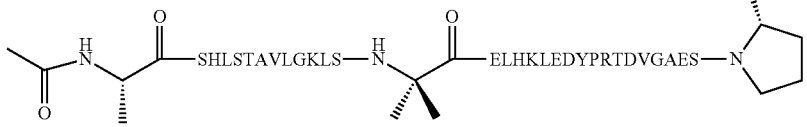

Accordingly, one of the compounds of the present disclosure is:

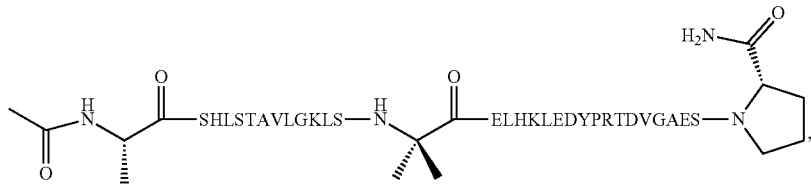

or a pharmaceutically acceptable salt thereof.

The compound comprising SEQ ID NO:1, or a pharmaceutically acceptable salt thereof, may further comprise one of more additional elements to extend the half-life of the compound. Elements that could be added to a compound comprising SEQ ID NO:1 for this purpose, with or without a linker and at any suitable position in the sequence, include the Fc portion of an immunoglobulin, fragments of the Fc portion of an immunoglobulin, human serum albumin (HSA), VHH, a variant of a VHH (variable domain of heavy chain antibodies) nanobody, fragments of human serum albumin, a $C_{16}$-$C_{20}$ monoacid, a $C_{16}$-$C_{20}$ diacid, and a polyethylene glycol (PEG) moiety or PEG alternative (e.g., polysarcosine). Other elements that could be added to a compound comprising SEQ ID NO:1 for this purpose, with or without a linker and at any suitable position in the sequence can also include, a $C_{16}$-$C_{22}$ monoacid, or a $C_{16}$-$C_{22}$ diacid, a $C_{18}$-$C_{20}$ monoacid, or a Cis-$C_{20}$ diacid.

In one embodiment of the presently disclosed compounds is a compound comprising SEQ ID NO:1 wherein the compound further comprises a fatty acid moiety with or without a linker.

In another embodiment, the presently disclosed compounds have an acetyl group ($CH_3CO$) on the alanine amino acid residue at the N-terminus of the peptide. This is signified herein by the phrase "Acetyl" and a dash preceding the N terminal amino acid residue in the peptide description. The presently disclosed compounds also have an amide group ($NH_2$) on the C terminal amino acid residue, proline. This is signified herein by the formula "$NH_2$" and a dash after the C terminal amino acid residue in the peptide description.

In another embodiment, a compound comprising SEQ ID NO:1 is acylated at any suitable amino acid in the sequence and consequently has an extended half-life. In another embodiment, a compound comprising SEQ ID NO:1 is acylated at the epsilon amino group on the lysine sidechain and consequently has an extended half-life. In a specific embodiment, a compound comprising SEQ ID NO:1 is acylated at the epsilon amino group on the lysine sidechain according to the formula 2-[2-(2-Amino-ethoxy)-ethoxy]-acetyl)$_2$-(γ-Glu)-CO—$(CH_2)_{18}$—$CO_2H$. Accordingly, one of the compounds of the present disclosure is Compound II, comprising the following sequence Acetyl-ASHL-STAVLGK((2-[2-(2-Amino-ethoxy)-ethoxy]-acetyl)$_2$-(γ-Glu)-CO—$(CH_2)_{18}$—$CO_2H$)LS-Aib-ELHKLEDYPRTDV-GAESP-$NH_2$ (SEQ ID NO:2), or a pharmaceutically acceptable salt thereof.

In a specific embodiment, a compound consisting of SEQ ID NO:1 is acylated at the epsilon amino group on the lysine sidechain according to the formula 2-[2-(2-Amino-ethoxy)-ethoxy]-acetyl)$_2$-(γ-Glu)-CO—$(CH_2)_{18}$—$CO_2H$. Accordingly, one of the compounds of the present disclosure is Compound II, consisting of the following sequence Acetyl-ASHLSTAVLGK((2-[2-(2-Amino-ethoxy)-ethoxy]-acetyl)$_2$-(γ-Glu)-CO—$(CH_2)_{18}$—$CO_2H$)LS-Aib-ELHKLEDYPRTDVGAESP-$NH_2$ (SEQ ID NO:2), or a pharmaceutically acceptable salt thereof. In a specific embodiment, a compound consisting essentially of SEQ ID NO:1 is acylated at the epsilon amino group on the lysine sidechain according to the formula 2-[2-(2-Amino-ethoxy)-ethoxy]-acetyl)$_2$-(γ-Glu)-CO—$(CH_2)_{18}$—$CO_2H$. Accordingly, one of the compounds of the present disclosure is Compound II, consisting essentially of the following sequence Acetyl-ASHLSTAVLGK((2-[2-(2-Amino-ethoxy)-ethoxy]-acetyl)$_2$-(γ-Glu)-CO—$(CH_2)_{18}$—$CO_2H$)LS-Aib-ELHKLEDYPRTDVGAESP-$NH_2$ (SEQ ID NO:2), or a pharmaceutically acceptable salt thereof. Below is a depiction of the structure of Compound II using the standard single letter amino acid codes with the exception of residues Acetyl-A1, K11, Aib14, and P32-$NH_2$, where the structures of these amino acid residues have been expanded.

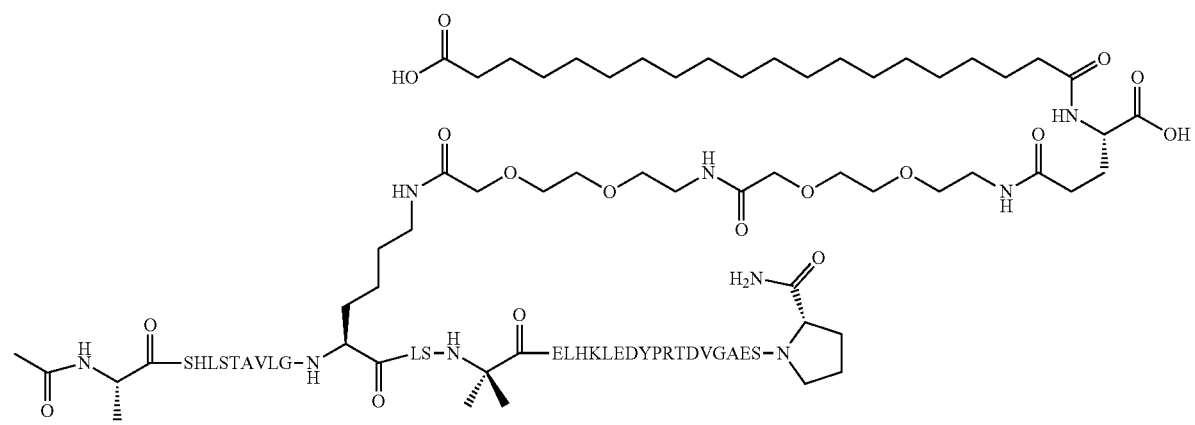

Accordingly, one of the compounds of the present disclosure is:

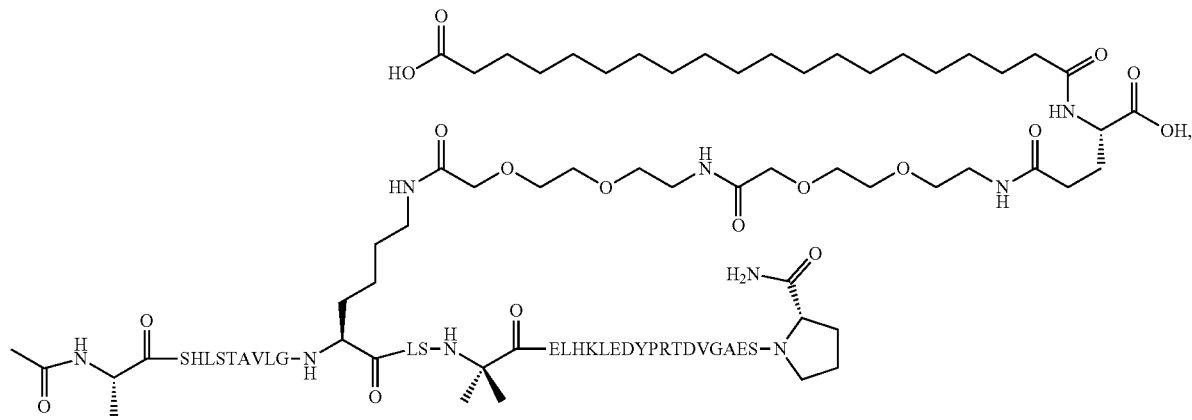

or a pharmaceutically acceptable salt thereof.

Another embodiment of the present disclosure provides a pharmaceutical composition comprising the compound comprising SEQ ID NO:1, or a pharmaceutically acceptable salt thereof, and one or more pharmaceutically acceptable excipients. Another embodiment of the present disclosure provides a pharmaceutical composition comprising the compound comprising SEQ ID NO:2, or a pharmaceutically acceptable salt thereof, and one or more pharmaceutically acceptable excipients.

Another embodiment of the present disclosure provides a method of treating diabetes in a patient in need thereof, comprising administering to the patient an effective amount of a compound comprising SEQ ID NO:1, or a pharmaceutically acceptable salt thereof. Another embodiment of the present disclosure provides a method of treating diabetes in a patient in need thereof, comprising administering to the patient an effective amount of a compound comprising SEQ ID NO:2, or a pharmaceutically acceptable salt thereof. A preferred embodiment of the present disclosure provides a method of treating Type 2 diabetes in a patient in need thereof, comprising administering to the patient an effective amount of a compound comprising SEQ ID NO:1, or a pharmaceutically acceptable salt thereof. Another preferred embodiment of the present disclosure provides a method of treating Type 2 diabetes in a patient in need thereof, comprising administering to the patient an effective amount of a compound comprising SEQ ID NO:2, or a pharmaceutically acceptable salt thereof. Another embodiment of the present disclosure provides a method of treating diabetes in a patient in need thereof, comprising administering to the patient a pharmaceutical composition comprising a compound comprising SEQ ID NO:1. Another embodiment of the present disclosure provides a method of treating diabetes in a patient in need thereof, comprising administering to the patient a pharmaceutical composition comprising a compound comprising SEQ ID NO:2. A preferred embodiment of the present disclosure provides a method of treating Type 2 diabetes in a patient in need thereof, comprising administering to the patient a pharmaceutical composition comprising a compound comprising SEQ ID NO:1. Another preferred embodiment of the present disclosure provides a method of treating Type 2 diabetes in a patient in need thereof, comprising administering to the patient a pharmaceutical composition comprising a compound comprising SEQ ID NO:2.

Another embodiment of the present disclosure provides a method of treating obesity in a patient in need thereof, comprising administering to the patient an effective amount of a compound comprising SEQ ID NO:1, or a pharmaceutically acceptable salt thereof. Another embodiment of the present disclosure provides a method of treating obesity in a patient in need thereof, comprising administering to the patient an effective amount of a compound comprising SEQ ID NO:2, or a pharmaceutically acceptable salt thereof. Another embodiment of the present disclosure provides a method of treating obesity in a patient in need thereof, comprising administering to the patient a pharmaceutical composition comprising a compound comprising SEQ ID NO:1. Another embodiment of the present disclosure provides a method of treating obesity in a patient in need thereof, comprising administering to the patient a pharmaceutical composition comprising a compound comprising SEQ ID NO:2.

Another embodiment of the present disclosure provides a method of treating dyslipidemia in a patient in need thereof, comprising administering to the patient an effective amount of a compound comprising SEQ ID NO:1, or a pharmaceutically acceptable salt thereof. Another embodiment of the present disclosure provides a method of treating dyslipidemia in a patient in need thereof, comprising administering to the patient an effective amount of a compound comprising SEQ ID NO:2, or a pharmaceutically acceptable salt thereof. Another embodiment of the present disclosure provides a method of treating dyslipidemia in a patient in need thereof, comprising administering to the patient a pharmaceutical composition comprising a compound comprising SEQ ID NO:1. Another embodiment of the present disclosure provides a method of treating dyslipidemia in a patient in need thereof, comprising administering to the patient a pharmaceutical composition comprising a compound comprising SEQ ID NO:2.

Another embodiment of the present disclosure provides a method of treating NASH in a patient in need thereof, comprising administering to the patient an effective amount of a compound comprising SEQ ID NO:1, or a pharmaceutically acceptable salt thereof. Another embodiment of the present disclosure provides a method of treating NASH in a patient in need thereof, comprising administering to the patient an effective amount of a compound comprising SEQ ID NO:2, or a pharmaceutically acceptable salt thereof.

Another embodiment of the present disclosure provides a method of treating NASH in a patient in need thereof, comprising administering to the patient a pharmaceutical composition comprising a compound comprising SEQ ID NO:1. Another embodiment of the present disclosure provides a method of treating NASH in a patient in need thereof, comprising administering to the patient a pharmaceutical composition comprising a compound comprising SEQ ID NO:2.

Another embodiment of the present disclosure provides a method of lowering food intake in a patient in need thereof, comprising administering to the patient an effective amount of a compound comprising SEQ ID NO:1, or a pharmaceutically acceptable salt thereof. Another embodiment of the present disclosure provides a method of lowering food intake in a patient in need thereof, comprising administering to the patient an effective amount of a compound comprising SEQ ID NO:2, or a pharmaceutically acceptable salt thereof. Another embodiment of the present disclosure provides a method of lowering food intake in a patient in need thereof, comprising administering to the patient a pharmaceutical composition comprising a compound comprising SEQ ID NO:1. Another embodiment of the present disclosure provides a method of lowering food intake in a patient in need thereof, comprising administering to the patient a pharmaceutical composition comprising a compound comprising SEQ ID NO:2.

Another embodiment of the present disclosure provides a method of lowering body weight in a patient in need thereof, comprising administering to the patient an effective amount of a compound comprising SEQ ID NO:1, or a pharmaceutically acceptable salt thereof. Another embodiment of the present disclosure provides a method of lowering body weight in a patient in need thereof, comprising administering to the patient an effective amount of a compound comprising SEQ ID NO:2, or a pharmaceutically acceptable salt thereof. Another embodiment of the present disclosure provides a method of lowering body weight in a patient in need thereof, comprising administering to the patient a pharmaceutical composition comprising a compound comprising SEQ ID NO:1. Another embodiment of the present disclosure provides a method of lowering body weight in a patient in need thereof, comprising administering to the patient a pharmaceutical composition comprising a compound comprising SEQ ID NO:2.

Another embodiment of the present disclosure provides a method of lowering blood glucose in a patient in need thereof, comprising administering to the patient an effective amount of a compound comprising SEQ ID NO:1, or a pharmaceutically acceptable salt thereof. Another embodiment of the present disclosure provides a method of lowering blood glucose in a patient in need thereof, comprising administering to the patient an effective amount of a compound comprising SEQ ID: 2, or a pharmaceutically acceptable salt thereof. Another embodiment of the present disclosure provides a method of lowering blood glucose in a patient in need thereof, comprising administering to the patient a pharmaceutical composition comprising a compound comprising SEQ ID NO:1. Another embodiment of the present disclosure provides a method of lowering blood glucose in a patient in need thereof, comprising administering to the patient a pharmaceutical composition comprising a compound comprising SEQ ID NO:2.

Another embodiment of the present disclosure provides a method of lowering triglycerides in a patient in need thereof, comprising administering to the patient an effective amount of a compound comprising SEQ ID NO:1, or a pharmaceutically acceptable salt thereof. Another embodiment of the present disclosure provides a method of lowering triglycerides in a patient in need thereof, comprising administering to the patient an effective amount of a compound comprising SEQ ID NO:2, or a pharmaceutically acceptable salt thereof. Another embodiment of the present disclosure provides a method of lowering triglycerides in a patient in need thereof, comprising administering to the patient a pharmaceutical composition comprising a compound comprising SEQ ID NO:1. Another embodiment of the present disclosure provides a method of lowering triglycerides in a patient in need thereof, comprising administering to a patient a pharmaceutical composition comprising a compound comprising SEQ ID NO:2.

Another embodiment of the present disclosure provides a method of treating diabetes in a patient in need thereof, wherein the compound comprising SEQ ID NO:1 is administered once weekly. Another embodiment of the present disclosure provides a method of treating diabetes in a patient in need thereof, wherein the compound comprising SEQ ID NO:2 is administered once weekly.

Another embodiment of the present disclosure provides a method of treating Type 2 diabetes in a patient in need thereof, wherein the compound comprising SEQ ID NO:1 is administered once weekly. Another embodiment of the present disclosure provides a method of treating Type 2 diabetes in a patient in need thereof, wherein the compound comprising SEQ ID NO:2 is administered once weekly.

Another embodiment of the present disclosure provides a method of treating obesity in a patient in need thereof, wherein the compound comprising SEQ ID NO:1 is administered once weekly. Another embodiment of the present disclosure provides a method of treating obesity in a patient in need thereof, wherein the compound comprising SEQ ID NO:2 is administered once weekly.

Another embodiment of the present disclosure provides a method of treating dyslipidemia in a patient in need thereof, wherein the compound comprising SEQ ID NO:1 is administered once weekly. Another embodiment of the present disclosure provides a method of treating dyslipidemia in a patient in need thereof, wherein the compound comprising SEQ ID NO:2 is administered once weekly.

Another embodiment of the present disclosure provides a method of treating NASH in a patient in need thereof, wherein the compound comprising SEQ ID NO:1 is administered once weekly. Another embodiment of the present disclosure provides a method of treating NASH in a patient in need thereof, wherein the compound comprising SEQ ID NO:2 is administered once weekly.

Another embodiment of the present disclosure provides a method of lowering food intake in a patient in need thereof, wherein the compound comprising SEQ ID NO:1 is administered once weekly. Another embodiment of the present disclosure provides a method of lowering food intake in a patient in need thereof, wherein the compound comprising SEQ ID NO:2 is administered once weekly.

Another embodiment of the present disclosure provides a method of lowering body weight in a patient in need thereof, wherein the compound comprising SEQ ID NO:1 is administered once weekly. Another embodiment of the present disclosure provides a method of lowering body weight in a patient in need thereof, wherein the compound comprising SEQ ID NO:2 is administered once weekly.

Another embodiment of the present disclosure provides a method of lowering blood glucose in a patient in need thereof, wherein the compound comprising SEQ ID NO:1 is administered once weekly. Another embodiment of the present disclosure provides a method of lowering blood glucose in a patient in need thereof, wherein the compound comprising SEQ ID NO:2 is administered once weekly.

Another embodiment of the present disclosure provides a method of lowering triglycerides in a patient in need thereof, wherein the compound comprising SEQ ID NO:1 is administered once weekly. Another embodiment of the present disclosure provides a method of lowering triglycerides in a patient in need thereof, wherein the compound comprising SEQ ID NO:2 is administered once weekly.

Another embodiment of the presently disclosed compounds provides a compound comprising SEQ ID NO:1, or a pharmaceutically acceptable salt thereof, for use in therapy. Another embodiment of the present disclosure provides a pharmaceutical composition comprising SEQ ID NO:1 for use in therapy. Another embodiment of the presently disclosed compounds provides a compound comprising SEQ ID NO:2, or a pharmaceutically acceptable salt thereof, for use in therapy. Another embodiment of the present disclosure provides a pharmaceutical composition comprising SEQ ID NO:2 for use in therapy.

Another embodiment of the presently disclosed compounds provides a compound comprising SEQ ID NO:1, or a pharmaceutically acceptable salt thereof, for use in the treatment of diabetes. Another embodiment of the present disclosure provides a pharmaceutical composition comprising SEQ ID NO:1 for use in the treatment of diabetes. Another embodiment of the presently disclosed compounds provides a compound comprising SEQ ID NO:2, or a pharmaceutically acceptable salt thereof, for use in the treatment of diabetes. Another embodiment of the present disclosure provides a pharmaceutical composition comprising SEQ ID NO:2 for use in the treatment of diabetes.

Another embodiment of the presently disclosed compounds provides a compound comprising SEQ ID NO:1, or a pharmaceutically acceptable salt thereof, for use in the treatment of Type 2 diabetes. Another embodiment of the present disclosure provides a pharmaceutical composition comprising SEQ ID NO:1 for use in the treatment of Type 2 diabetes. Another embodiment of the presently disclosed compounds provides a compound comprising SEQ ID NO:2, or a pharmaceutically acceptable salt thereof, for use in the treatment of Type 2 diabetes. Another embodiment of the present disclosure provides a pharmaceutical composition comprising SEQ ID NO:2 for use in the treatment of Type 2 diabetes.

Another embodiment of the presently disclosed compounds provides a compound comprising SEQ ID NO:1, or a pharmaceutically acceptable salt thereof, for use in the treatment of obesity. Another embodiment of the present disclosure provides a pharmaceutical composition comprising SEQ ID NO:1 for use in the treatment of obesity. Another embodiment of the presently disclosed compounds provides a compound comprising SEQ ID NO:2, or a pharmaceutically acceptable salt thereof, for use in the treatment of obesity. Another embodiment of the present disclosure provides a pharmaceutical composition comprising SEQ ID NO:2 for use in the treatment of obesity.

Another embodiment of the presently disclosed compounds provides a compound comprising SEQ ID NO:1, or a pharmaceutically acceptable salt thereof, for use in the treatment of dyslipidemia. Another embodiment of the present disclosure provides a pharmaceutical composition comprising SEQ ID NO:1 for use in the treatment of dyslipidemia. Another embodiment of the presently disclosed compounds provides a compound comprising SEQ ID NO:2, or a pharmaceutically acceptable salt thereof, for use in the treatment of dyslipidemia. Another embodiment of the present disclosure provides a pharmaceutical composition comprising SEQ ID NO: 2, for use in the treatment of dyslipidemia.

Another embodiment of the presently disclosed compounds provides a compound comprising SEQ ID NO:1, or a pharmaceutically acceptable salt thereof, for use in the treatment of NASH. Another embodiment of the present disclosure provides a pharmaceutical composition comprising SEQ ID NO:1 for use in the treatment of NASH. Another embodiment of the presently disclosed compounds provides a compound comprising SEQ ID NO:2, or a pharmaceutically acceptable salt thereof, for use in the treatment of NASH. Another embodiment of the present disclosure provides a pharmaceutical composition comprising SEQ ID NO:2 for use in the treatment of NASH.

Another embodiment of the present disclosure provides for the use of a compound comprising SEQ ID NO:1, or a pharmaceutically acceptable salt thereof, in the manufacture of a medicament for the treatment of diabetes. Another embodiment of the present disclosure provides for the use of a compound comprising SEQ ID NO:2, or a pharmaceutically acceptable salt thereof, in the manufacture of a medicament for the treatment of diabetes. A preferred embodiment of the present disclosure provides for the use of a compound comprising SEQ ID NO:1, or a pharmaceutically acceptable salt thereof, in the manufacture of a medicament for the treatment of Type 2 diabetes. In another preferred embodiment of the present disclosure provides for the use of a compound comprising SEQ ID NO:2, or a pharmaceutically acceptable salt thereof, in the manufacture of a medicament for the treatment of diabetes.

Another embodiment of the present disclosure provides for the use of a compound comprising SEQ ID NO:1, or a pharmaceutically acceptable salt thereof, in the manufacture of a medicament for the treatment of obesity. Another embodiment of the present disclosure provides for the use of a compound comprising SEQ ID NO:2, or a pharmaceutically acceptable salt thereof, in the manufacture of a medicament for the treatment of obesity.

Another embodiment of the present disclosure provides for the use of a compound comprising SEQ ID NO:1, or a pharmaceutically acceptable salt thereof, in the manufacture of a medicament for the treatment of dyslipidemia. Another embodiment of the present disclosure provides for the use of a compound comprising SEQ ID NO:2, or a pharmaceutically acceptable salt thereof, in the manufacture of a medicament for the treatment of dyslipidemia.

Another embodiment of the present disclosure provides for the use of a compound comprising SEQ ID NO:1, or a pharmaceutically acceptable salt thereof, in the manufacture of a medicament for the treatment of NASH. Another embodiment of the present disclosure provides for the use of a compound comprising SEQ ID NO:2, or a pharmaceutically acceptable salt thereof, in the manufacture of a medicament for the treatment of NASH.

Another embodiment of the presently disclosed compounds is the compound of SEQ ID NO:1 where the half-life ($t_{1/2}$) is extended.

Another embodiment of the present disclosure is a method of treating a condition in patient in need thereof, selected from the group consisting of: diabetes, obesity, NASH, and/or dyslipidemia, comprising administering to the patient an effective amount of a compound comprising SEQ ID NO:1, or a pharmaceutically acceptable salt thereof, in combination with an effective amount of an incretin or incretin analog. Another embodiment of the present disclosure is a method of treating a condition in a patient in need thereof, selected from the group consisting of: diabetes, obesity, NASH, and/or dyslipidemia, comprising administering to the patient an effective amount of a compound comprising SEQ ID NO:2, or a pharmaceutically acceptable salt thereof, in combination with an effective amount of an incretin or incretin analog.

In a particular embodiment of the present disclosure is a method of treating a condition in patient in need thereof, selected from a group consisting of: diabetes, obesity, NASH, and/or dyslipidemia, comprising administering to a patient in need of such treatment an effective amount of a compound comprising SEQ ID NO:1, or a pharmaceutically acceptable salt thereof, in combination with a GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with a GLP-1 agonist selected from the group consisting of compounds comprising Compound III (SEQ ID NO:6), Compound VIII (SEQ ID NO:12), or Compound IX (SEQ ID NO:13). In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a GLP-1 agonist selected from the group consisting of compounds comprising Compound III (SEQ ID NO:6), Compound VIII (SEQ ID NO:12), or Compound IX (SEQ ID NO:13).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with a dual GIP/GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with a dual GIP/GLP-1 agonist selected from the group consisting compounds comprising Compound VI (SEQ ID NO:9) and Compound VII (SEQ ID NO:10). In a particular embodiment of the present disclosure is a method of treating a patient with diabetes, obesity, NASH, and/or dyslipidemia, comprising administering to a patient in need of such treatment an effective amount of a compound comprising SEQ ID NO:2 in combination with a dual GIP/GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a dual GIP/GLP-1 agonist selected from the group consisting of compounds comprising Compound VI (SEQ ID NO:9) and Compound VII (SEQ ID NO:10).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with a triagonist of glucagon, GIP, and GLP-1. In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a triagonist of glucagon, GIP, and GLP-1. In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with a triagonist of glucagon, GIP, and GLP-1 comprising Compound V (SEQ ID NO:8). In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a triagonist of glucagon, GIP, and GLP-1 comprising Compound V (SEQ ID NO:8).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with an analog of oxyntomodulin. In a particular embodiment of the presently disclosed compounds is a method of treating a patient with diabetes, obesity, NASH, and/or dyslipidemia, comprising administering to a patient in need of such treatment an effective amount of a compound comprising SEQ ID NO:2 in combination with an analog of oxyntomodulin. In a particular embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with an analog of oxyntomodulin comprising Compound IV (SEQ ID NO:7). In a particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with an analog of oxyntomodulin comprising Compound IV (SEQ ID NO:7).

Another embodiment of the present disclosure is a method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with an incretin or incretin analog wherein the compound comprising SEQ ID NO:1, or a pharmaceutically acceptable salt thereof, and the incretin or incretin analog are administered simultaneously. Another embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with an incretin or incretin analog wherein the compound comprising SEQ ID NO:2, or a pharmaceutically acceptable salt thereof, and the incretin or incretin analog are administered simultaneously.

Another embodiment of the present disclosure is the method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with an incretin or incretin analog wherein the compound comprising SEQ ID NO:1, or a pharmaceutically acceptable salt thereof, is administered prior to the administration of the incretin or incretin analog. Another embodiment of the present disclosure is the method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with an incretin or incretin analog wherein the compound comprising SEQ ID NO:2, or a pharmaceutically acceptable salt thereof, is administered prior to the administration of the incretin or incretin analog.

Another embodiment of the present disclosure is the method of treating a patient with diabetes, obesity, NASH, and/or dyslipidemia, comprising administering to a patient in need of such treatment an effective amount of a compound comprising SEQ ID NO:1, or a pharmaceutically acceptable salt thereof, in combination with an incretin or incretin analog wherein the incretin or incretin analog is administered prior to the administration of the compound comprising SEQ ID NO:1, or a pharmaceutically acceptable salt thereof. Another embodiment of the present disclosure is the method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with an incretin or incretin analog wherein the incretin or incretin analog is administered prior to the administration of the compound comprising SEQ ID NO:2, or a pharmaceutically acceptable salt thereof.

Another embodiment of the present disclosure is the compound comprising SEQ ID NO:1 for use in separate, simultaneous, or sequential combination with an incretin or incretin analog for the treatment of diabetes, obesity, NASH, and/or dyslipidemia. Another embodiment of the present disclosure is the compound comprising SEQ ID NO:2 for use in separate, simultaneous, or sequential combination with an incretin or incretin analog for the treatment of diabetes, obesity, NASH, and/or dyslipidemia.

Another embodiment of the present disclosure provides for the use of the compound comprising SEQ ID NO:1 in the manufacture of a medicament for the treatment of diabetes. Another embodiment of the present disclosure provides for the use of the compound comprising SEQ ID NO:2 in the manufacture of a medicament for the treatment of diabetes.

Another embodiment of the present disclosure provides for the use of the compound comprising SEQ ID NO:1 in the manufacture of a medicament for the treatment of Type 2 diabetes. Another embodiment of the present disclosure provides for the use of the compound comprising SEQ ID NO:2 in the manufacture of a medicament for the treatment of Type 2 diabetes.

Another embodiment of the present disclosure provides for the use of the compound comprising SEQ ID NO:1 in the manufacture of a medicament for the treatment of obesity. Another embodiment of the present disclosure provides for the use of the compound comprising SEQ ID NO:2 in the manufacture of a medicament for the treatment of obesity.

Another embodiment of the present disclosure provides for the use of the compound comprising SEQ ID NO:1 in the manufacture of a medicament for the treatment of dyslipidemia. Another embodiment of the present disclosure provides for the use of the compound comprising SEQ ID NO:2 in the manufacture of a medicament for the treatment of dyslipidemia.

Another embodiment of the present disclosure provides for the use of the compound comprising SEQ ID NO:1 in the manufacture of a medicament for the treatment of NASH. Another embodiment of the present disclosure provides for the use of the compound comprising SEQ ID NO:2 in the manufacture of a medicament for the treatment of diabetes.

Unless defined otherwise, all technical and scientific terms used herein have the same meaning as commonly understood by one of skill in the art to which the disclosure pertains. Although any methods and materials similar to or equivalent to those described herein can be used in the practice or testing of dual amylin and calcitonin receptor agonists, pharmaceutical compositions, pharmaceutical combinations, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "analog" refers to a compound, such as a synthetic peptide or polypeptide, that activates a target receptor and that elicits at least one in vivo or in vitro effect elicited by a native agonist for that receptor.

The term "combination" as used herein means compounds presently disclosed may be used in simultaneous, separate or sequential combination with one or more additional therapeutic agents useful for inducing weight loss, treating diabetes, conditions related to diabetes, obesity, NASH, and/or dyslipidemia. Non-limiting examples of the additional therapeutic agents that can be combined with the claimed compounds include: insulin or insulin analogs; incretin compounds or incretin analogs, such as glucagon-like-peptide-1 (GLP-1) or GLP-1 analogs, gastric inhibitory polypeptide (GIP) or GIP analogs, oxyntomodulin or oxyntomodulin analogs; dual GIP/GLP-1 agonists; Gcg/GIP/GLP-1 triagonists (triagonists of glucagon, GIP, and GLP-1); or combinations of any of the foregoing agents. The claimed compounds and the additional therapeutic agent(s) can be co-administered through the same delivery route and device such as a single pill, capsule, tablet, or injectable formulation; or separately administered either at the same time in separate delivery devices or routes; or administered sequentially.

The term "diabetes" refers to a disease in which the body's ability to produce or respond to the hormone insulin is impaired, resulting in abnormal metabolism of carbohydrates and elevated levels of glucose in the blood and urine. As used herein, the term diabetes may refer to a chronic condition that affects the way the body processes blood sugar, or glucose, e.g., type 2 diabetes mellitus (T2DM); a chronic condition in which the pancreas produces little or no insulin, e.g., type 1 diabetes mellitus (T1DM); a condition in which blood sugar is high, but not high enough to be type 2 diabetes, e.g., pre-diabetes; a form of high blood sugar affecting pregnant women, e.g., gestational diabetes.

The term "dyslipidemia" as used herein refers to a disorder of lipoprotein metabolism, including lipoprotein over-production or deficiency. Dyslipidemias may be manifested by elevation of the total cholesterol, low-density lipoprotein (LDL) cholesterol and triglyceride concentrations, and/or a decrease in the high-density lipoprotein (HDL) concentration in the blood. Dyslipidemia may or may not develop in connection with diabetes.

The term "incretin" as used herein refers to a group of endogenous metabolic hormones that are excreted from the enteroendrocrine cells in the stomach and pancreas to stimulate a decrease in blood glucose, typically via regulation of the amount of insulin that is secreted after meals. The term "incretin analog" as used herein refers to a group of synthetic incretin mimetics which are physiologically similar to incretins. Further, "incretin analogs" may have favorable pharmacological properties compared to endogenous incretins.

The term "treatment" or "treating" as used herein refers to the management and care of a patient having a condition for which amylin and calcitonin receptor peptide agonist administration is indicated for the purpose of combating or alleviating symptoms and complications of the condition. Treating includes administering a compound or a pharmaceutical composition containing a compound of the presently disclosed compounds to a patient in need thereof to prevent the onset of symptoms or complications, alleviating the symptoms or complications, or eliminating the disease, condition, or disorder. Preferably treating includes administering a compound or pharmaceutical composition containing a compound of the presently disclosed compounds to a patient in need thereof to result in a net loss of body weight, a reduction in food intake, a reduction in blood glucose levels and/or a reduction in triglyceride levels. The patient to be treated is an animal, and preferably a human being.

As used herein, the term "effective amount" refers to the amount or dose of a compound of the presently disclosed compounds or a pharmaceutical composition containing the presently disclosed compounds, upon which single or multiple dose administration to the patient will elicit the biological or medical response or desired therapeutic effect being sought by a health care professional. Preferably an effective amount of a compound or pharmaceutical composition containing a compound of the presently disclosed compounds administered to a patient in need thereof would result in a net loss of body weight, a reduction in food intake, a reduction in blood glucose levels and/or a reduction in triglyceride levels. A dose can include a higher initial loading dose, followed by a lower dose.

The term "patient," refers to an animal, and preferably to a human. In certain embodiments, the patient, preferably a human, is further characterized with a disease, disorder or condition that would benefit from administration of a compound that agonizes both the amylin and calcitonin receptors. Pharmaceutical compositions comprising the presently disclosed compounds may be administered orally or parenterally to patients in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump. Embodiments of the presently disclosed compounds provide pharmaceutical compositions suitable for administration to a patient comprising administering to a patient in need thereof a therapeutically effective amount of a compound presently disclosed and one or more pharmaceutically acceptable excipients. Such pharmaceutical compositions may be prepared by any of a variety of techniques using conventional excipients for pharmaceutical products which are well known in the art. (Remington's Pharmaceutical Sciences, 21st Edition, University of the Sciences in Philadelphia, Philadelphia, Pa., USA (2006)).

The term "NASH" as used herein stands for non-alcoholic steatohepatitis, aka fatty liver disease. "NASH" also refers to liver inflammation and damage caused by a buildup of fat in the liver. "NASH" also refers to a subtype of nonalcoholic fatty liver disease ("NAFLD). In some embodiments, "NASH" may be synonymous with "NAFLD."

The term "obesity" as used herein refers to a disorder involving excess body fat that increases the risk of health problems. The term "obesity" also refers to weight that is higher than what is considered a healthy weight for a given height. The term "obesity" also refers to a BMI greater than 30.0. As used herein, body mass index (BMI) refers to a person's weight in kilograms divided by the square of height in meters.

Certain abbreviations are defined as follows: "Aib" refers to 2-aminoisobutyric acid; "AMY1" refers to amylin receptor 1; "cAMP" refers to cyclic adenosine monophosphate; "CT" refers to calcitonin; "DCM" refers to dichloromethane; "DIEA" refers to diisopropylethylamine; "DIO" refers to diet induced obese; "DMF" refers to dimethylformamide; "FBS" refers to fetal bovine serum; "GPCR" refers G-protein coupled receptor(s); "HEPES" refers to 4-(2-hydroxyethyl)-1-piperazineethanesulfonic acid; "HTRF" refers to homogeneous time resolved fluorescence; "IBMX" refers to 1-methyl-3-isobutylxanthine; "Mtt" refers to 4-methyltrityl; "PBMC" refers to peripheral blood mononuclear cell; "PyAOP" refers to (7-azabenzotriazol-1-yloxy)tripyrrolidinophosphonium hexafluorophosphate; "RP-HPLC" refers to reverse phase high pressure liquid chromatography; and "TFA" refers to trifluoroacetic acid.

EXAMPLE 1: PREPARATION AND PURIFICATION OF COMPOUND I AND COMPOUND II

Compound I and Compound II are made according to the following steps. First, Compound I is synthesized using Fluorenyimethyloxycarbonyl (Fmoc)/tert-Butyl (t-Bu) chemistry on a Symphony 12-channel multiplex peptide synthesizer (Protein Technologies, Inc. Tucson, Ariz.).

Polystyrene Rink Amide AM LL resin (Novabiochem, sub: 0.33 meq/g, 100-200 mesh, Cat4855045) is used for the synthesis at 0.13 mmol scale. Standard sidechain protecting groups are used. Fmoc-Lys(Mtt)-OH is used for the lysine at position 11. Fmoc groups are removed prior to each coupling step (2×7 minutes) using 20% piperidine in DMF. AH amino acid couplings are performed for 30 minutes at 50° C. using an equal molar ratio of Fmoc amino acid, diisopropylcarbodiimide and Oxyma, at a 7.7-fold molar excess over the theoretical peptide loading. N-termini is acetylated with 5% acetic anhydride, 5% DIEA in DMF for 30 minutes. Below is a schematic of Compound I (SEQ ID NO:1).

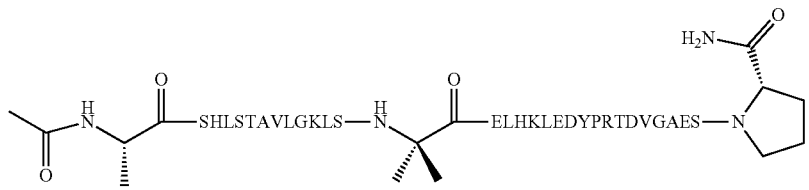

Then, the resin is thoroughly washed with DCM for 6 times to remove residual DMF. The Mtt protecting group on the lysine at position 11 is selectively removed from the peptide resin using two treatments of 30% hexafluoroisopropanol (Oakwood Chemicals) in DCM (2×40-minute treatment).

Synthesis of Compound II is made according to the following steps. Subsequent attachment of the fatty acid-linker moiety is accomplished by coupling of 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-Glu-OtBu, Ark Pharm, Inc.), mono-OtBu-eicosanoic acid (WuXi AppTec, Shanghai, China). 3-Fold excess of reagents (AA: PyAOP: DIEA=1:1:1 mol/mol) are used for each coupling that is 1-hour long.

After the synthesis is complete, the peptide resin is washed with DCM, and then thoroughly air-dried. The dry resin is treated with 10 mL of cleavage cocktail (TFA: water: triisopropylsilane, 95:2.5:2.5 v/v) for 2 hours at room temperature. The resin is filtered off, washed twice each with 2 mL of neat TFA, and the combined filtrates are treated with 4-fold cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times and dried in vacuo. The crude peptide is solubilized in 20% acetonitrile/20% acetic acid/60% water and purified by RP-HPLC on a Waters Xselect Peptide CSH C18 prep column 130A 5um 19×150 mm PN 186007021) with a linear gradient using 100% acetonitrile and 0.1% TFA/water buffer system (20-40% acetonitrile in 60 min), The purity of peptide is assessed using analytical RP-HPLC and pooling criteria is >95%. The main pool purity of Compound I is found to be >99.0%. Subsequent lyophilization of the final main product pool yields the lyophilized peptide TFA salt. The molecular weight is determined by LC/MS. Average MW=3447.8 Da. Expected mass: (M+3H): 1150.3, found 1150.0.

The main pool purity of Compound II is found to be >98.0%. Subsequent lyophilization of the final main product pool yields the lyophilized peptide TFA salt. The molecular weight is determined by LC/MS. Average MW=4191.8 Da. Expected mass: (M+3H): 1398.2, found 1398.2. Below is a schematic of Compound II (SEQ ID NO:2).

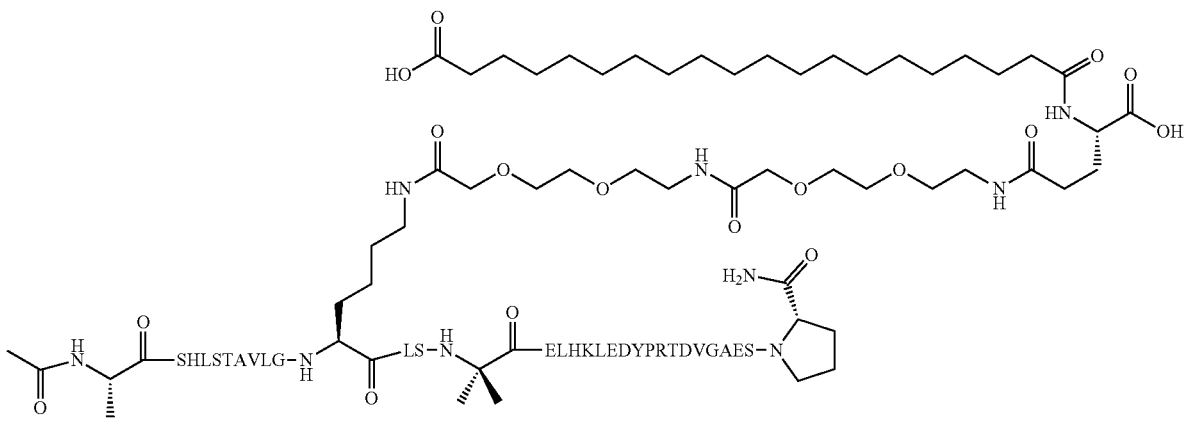

Similar processes to those described above and known to those of skill in the art may be used to synthesize the peptide backbone, conjugate the fatty acid-linker moiety, examine the purity, and confirm the molecular weight of the inventive compound described herein.

EXAMPLE 2: IN VITRO FUNCTIONAL ACTIVITY

The AMY1 and CT receptors are GPCRs that are functionally coupled to Gαs proteins. Stimulation of these receptors results in an increased production of intracellular cAMP, which can be detected using standard in vitro technologies. Human AMY1 or CT receptors are stably expressed in human urinary bladder cells (UM-UC-3) cells under control of a pcDNA (CALCR) or pCMV piggybac (RAMP1) expression vector. AMY1 cells are cultured in MEM 1× (Corning) supplemented with 10% FBS, 1% antibiotic/antimycotic solution, 1 mM sodium pyruvate, 1×MEM NEAA, 1× GlutaMAX-I, 200 μg/mL hygromycin B, and 0.4 μg/mL puromycin. CT cells are cultured in the same medium except that it lacks the puromycin. Cultured cells are grown to 70% confluency, and then incubated overnight with fresh medium.

On the assay day, 10 μL of assay buffer (phenol red free MEM (Corning, cat #17-305-CV), 0.1% casein, 0.5 mM IBMX, 5 mM HEPES, pH 7.4) is dispensed into each well of white poly-D-lysine coated 384-well plates (Corning cat #354661). Peptides diluted in DMSO are added (200 nL/well) in a 1:3 dilution series using ECHO acoustic liquid handler (Beckman). Cultured cells are detached with TrypLE Express (Gibco), resuspended in assay buffer, and 10μL containing 1200 cells/well (hCT) or 1500 cells/well (hAMY1) are dispensed into each well. The plates are incubated at room temperature for 1 hour.

The amount of intracellular cAMP is quantitated using HTRF technology (Homogeneous Time Resolved Fluorescence; Cisbio) as per vendor instructions. Briefly, 10 μL cAMP-d2 conjugate and 10 μL anti-cAMP-cryptate conjugate in lysis buffer are incubated with the treated cells at room temperature for 60 min. The HTRF signal is immediately detected using an Envision plate reader (Perkin-Elmer) to calculate the ratio of fluorescence at 665 to 620 nm. The raw data are converted to cAMP amount (pmole/well) using a cAMP standard curve generated for each experiment. Relative $EC_{50}$ values are calculated from the top-bottom range of the concentration response curve defined using 1 nM salmon CT (Bachem) as the maximum and buffer alone as the minimum with a four-parameter logistic curve fitting program (Genedata Screener® v12.0.4). The compounds of the present application show activity at the amylin and calcitonin receptors as shown in Table 1.

TABLE 1

Activity of Compounds I and II at Amylin and Calcitonin Receptors.

| Compound | hAMY1 cAMP EC50 (pM) | hCT cAMP EC50 (pM) |
|---|---|---|
| Compound I | 49.3 ± 8.04 (n = 4) | 31.7 ± 5.8 (n = 3) |
| Compound II | 49.4 ± 5.14 (n = 7) | 40.9 ± 14.7 (n = 4) |
| Pramlintide | 44.0 ± 4.79 (n = 22) | 2320 ± 408 (n = 18) |
| Human calcitonin | 397 ± 63.5 (n = 7) | 106 ± 20.5 (n = 6) |

EXAMPLE 3: IN VIVO EFFICACY IN NORMAL RAT MODELS

Male Sprague Dawley (SD) rats from Envigo Laboratories weighing approximately 300 grams are used to evaluate the effects of Compound II on acute reductions in food intake and body weight loss in vivo during a 96-hour evaluation study. The rats are maintained under approved Animal Care and Use protocols for Lilly Research Laboratories and are housed individually on a 12 hour reverse light cycle from 10 p.m. to 10 a.m. The morning of the study, baseline animal body and food weights are measured and vehicle (20 mM Tris pH8, 50 mg/mL D-mannitol, 0.02% PS80) or Compound II (SEQ ID NO:2) alone in vehicle (20 mM Tris pH8, 50 mg/mL D-mannitol, 0.02% PS80) are subcutaneously administered at different doses.

Animal body and food weights are measured at 24-, 48-, 72- and 96-hours post-administration. The daily food intake and the percent decrease in body weight are calculated. The results are listed below in Tables 2 and 3. All data is indicated as the mean daily food intake and percent body weight decrease. As demonstrated by the results, Compound II has an effect to reduce food consumption and reduce body weight acutely and in a dose-dependent manner. Also, even very low doses show efficacy in lowering food intake and body weight.

TABLE 2

Effect of Compound II on Daily Food Intake in Sprague-Dawley Rats.

| Dose | Daily Food Intake (grams) | | | | |
|---|---|---|---|---|---|
| (nmol/kg) | 0 h | 24 h | 48 h | 72 h | 96 h |
| Control | 0.00 | 18.58 | 20.42 | 19.88 | 20.12 |
| 0.1 | 0.00 | 16.12 | 19.65 | 19.93 | 21.60 |
| 0.3 | 0.00 | 15.55 | 18.65 | 20.47 | 21.32 |
| 1 | 0.00 | 13.72 | 16.92 | 19.77 | 21.03 |
| 3 | 0.00 | 5.32 | 10.22 | 14.88 | 18.78 |
| 10 | 0.00 | 2.77 | 0.87 | 9.62 | 15.45 |
| 30 | 0.00 | 3.75 | 0.30 | 5.67 | 14.85 |

TABLE 3

Effect of Compound II on % Change in Body Weight in Sprague-Dawley Rats.

| Dose | % Change in Body Weight | | | | |
|---|---|---|---|---|---|
| (nmol/kg) | 0 h | 24 h | 48 h | 72 h | 96 h |
| Control | 0.00 | −0.38 | 0.54 | 1.27 | 1.61 |
| 0.1 | 0.00 | −0.89 | −0.16 | 0.61 | 2.06 |
| 0.3 | 0.00 | −0.91 | −0.64 | 0.39 | 1.50 |
| 1 | 0.00 | −1.82 | −1.44 | −0.38 | 0.57 |
| 3 | 0.00 | −3.63 | −4.68 | −4.66 | −3.26 |
| 10 | 0.00 | −5.67 | −10.02 | −9.88 | −8.95 |
| 30 | 0.00 | −6.24 | −11.60 | −12.43 | −11.74 |

EXAMPLE 4: IN VIVO EFFICACY IN DIET INDUCED OBESE (DIO) RATS

This study is conducted to investigate the effect of Compound II for diabetes and/or obesity conditions in DIO rats. Diet-induced obese (DIO) male Long Evans (Envigo) rats 24 to 30 weeks old, maintained on a calorie rich diet since arrival at Lilly (TD95217; Teklad, Madison, Wis.), are used in the following studies. Animals are individually housed in a temperature-controlled (24° C.) facility with 12-hour light/dark cycle (lights on 2200) and free access to food (TD95217) and water.

The rats are randomized according to their body weight, so that each experimental group of animals would have similar body weight. The body weights range from 514 to 710 grams.

Each groups contains five rats. Vehicle and Compound II (0.1 and 100 nmol/kg) dissolved in vehicle (Tris pH8, (50 mg/mL D-mannitol)+0.02% ps80) are administered by subcutaneous (SC) injection (1 mL/kg) to ad libitum fed DIO rats 30 to 60 minutes prior to the onset of the dark cycle every 3 days for 15 days. SC injections are made on Day 1, 4, 7, 10 and 13. Body weight and food intake are measured daily throughout the study. Absolute changes in body weight are calculated by subtracting the body weight of the same animal prior to the first injection of molecule. Body composition was assessed by quantitative nuclear magnetic resonance (QMNR, EchoMRI LLC, Houston, Tex.) on Days −1 (one day prior to treatment) and 15.

At the end of the study, blood is collected to measure blood glucose and plasma insulin. Blood glucose is measured by AccuChek glucometers (Roche, Indianapolis, Ind.). Insulin is measured by ELISA (MSD, Rockville, Md.).

All data are presented as mean±SEM of 5 animals per group. Statistical analysis is performed using repeated measures ANOVA, followed by Dunnett's method for multiple comparisons. Significant differences are identified at $p<0.05$.

Compound II reduces body weight and food intake in male DIO rats in a dose-dependent manner. Reduced body weight is likely primarily due to reduction in fat mass. In addition to substantial weight loss, reduced serum glucose and reduced insulin are observed with treatment using Compound II in a dose-dependent manner as shown in Tables 4 and 5.

Body composition measurements are done on Day 0 and Day 14. The change from the initial measurement is presented as Measurement on Day 0-Measurement on Day 14. All data are presented as mean±SEM of 5 animals per group from Day 14. Statistical analysis is performed using repeated measures ANOVA, followed by Dunnett's method for multiple comparisons. Significant differences are identified at $p<0.05$.

TABLE 4

The effect of Compound II on body weight, cumulative food intake and fat mass in DIO rats on Day 15

| Compound (dose) | Body Weight Change (g) | Cumulative Food Intake (g) | Fat Mass Change (g) |
| --- | --- | --- | --- |
| Vehicle (1 mL/kg, SC) | 8.36 ± 3.69 | 236.38 ± 6.08 | 3.58 ± 1.0 |
| Compound II (0.1 nmol/kg) | 4.32 ± 1.66 | 235.58 ± 6.34 | 4.93 ± 2.96 |
| Compound II (0.3 nmol/kg) | −18.74 ± 3.31* | 197.14 ± 14.35 | −10.62 ± 2.80* |
| Compound II (1 nmol/kg) | −38.30 ± 5.67* | 163.56 ± 13.40* | −22.42 ± 4.74* |
| Compound II (3 nmol/kg) | −59.84 ± 5.32* | 125.70 ± 12.36* | −38.09 ± 3.64* |
| Compound II (10 nmol/kg) | −73.06 ± 4.27* | 110.12 ± 11.24* | −43.26 ± 0.81* |
| Compound II (30 nmol/kg) | −77.24 ± 3.41* | 103.14 ± 13.53* | −41.94 ± 6.05* |
| Compound II (100 nmol/kg) | −85.84 ± 3.78* | 89.36 ± 10.45* | −40.77 ± 3.46* |

*Significant differences are identified at $p < 0.05$

TABLE 5

The effect of Compound II treatment on fasting blood glucose, insulin, insulin resistance index (HOMA-IR = fasting glucose[mmol/L] X Fasting Insulin [µU/ml])/22.5) and glucose area under the curve for 60 minutes (AUC 60 min) during oral glucose tolerance test (OGTT) in DIO rats

| Compound (dose) | Fasting Glucose [FG](mmol/L) | Fasting Insulin [FI] (µU/ml) | HOMA-IR [(FG X FI)/22.5] | Glucose (mg/dL) AUC (60 min) during OGTT |
| --- | --- | --- | --- | --- |
| Vehicle (1 ml/kg, SC) | 7.10 ± 0.40 | 39.08 ± 4.77 | 12.52 ± 1.95 | 14582.25 ± 1299.63 |
| Compound II (0.1 nmol/kg) | 6.94 ± 0.22 | 41.68 ± 5.13 | 12.98 ± 1.69 | 14638.50 ± 607.28 |
| Compound II (0.3 nmol/kg) | 6.50 ± 0.13 | 35.06 ± 4.89 | 10.22 ± 1.56 | 11367.75 ± 486.94* |
| Compound II (1 nmol/kg) | 6.94 ± 0.43 | 18.38 ± 3.53* | 5.82 ± 1.31* | 11367.75 ± 703.77* |
| Compound II (3 nmol/kg) | 6.78 ± 0.28 | 23.84 ± 2.15* | 7.26 ± 0.93* | 11189.25 ± 657.87* |
| Compound II (10 nmol/kg) | 7.04 ± 0.20 | 28.08 ± 2.51 | 8.72 ± 0.62 | 10959.75 ± 507.17* |
| Compound II (30 nmol/kg) | 6.02 ± 0.38 | 15.16 ± 3.63* | 4.02 ± 0.91* | 9936.00 ± 752.37* |
| Compound II (100 nmol/kg) | 5.86 ± 0.32* | 11.92 ± 2.46* | 3.20 ± 0.76* | 10014.00 ± 538.58* |

*Significant differences are identified at $p < 0.05$

EXAMPLE 5: PHARMACOKINETIC BEHAVIOR OF COMPOUND II

Plasma concentration of Compound II is determined by a qualified Liquid Chromatography Mass Spectrometry (LC/MS) method at Q Squared Solutions BioSciences LLC, Ithaca, N.Y. Compound II and an analog as an internal standard are extracted from 100% species-specific plasma using protein precipitation followed by solid phase extraction. The intact mass of Compound II which includes peptide plus acyl chain is detected by a Q-Exactive Orbitrap™ mass spectrometer.

In a monkey pharmacokinetics study, male and female Cynomolgus monkeys are administered a single subcutaneous dose of 20 nmol/kg (0.084 mg/kg) of Compound II in Tris-mannitol buffer (pH 8.0) at a volume of 0.2 mL/kg. Blood is collected predose and at 1, 3, 6, 12, 24, 48, 72, 96, 120, 144, 168, 240, 336, 408, 504 hours postdose for pharmacokinetic characterization. The results are shown in Table 6.

TABLE 6

Individual and Mean Plasma Pharmacokinetic Parameters Following a Single 20 nmol/kg Subcutaneous Dose of Compound II to Male and Female Cynomolgus Monkeys

| Compound | Animal ID | $T_{1/2}$ (hr) | Tmax (hr) | Cmax (nmol/L) | $AUC_{0-inf}$ (hr * nmol/L) | CL/F (mL/hr/kg) |
|---|---|---|---|---|---|---|
| Compound II | P0001 | 185 | 12 | 198 | 50355 | 0.40 |
| | P0101 | 170 | 72 | 138 | 44678 | 0.45 |
| | Mean | 178 | 42 | 168 | 47516 | 0.42 |

Abbreviations:
$T_{1/2}$ = half-life,
$T_{max}$ = time to maximum concentration,
$C_{max}$ = maximum observed plasma concentration,
$AUC_{0-inf}$ = area under the curve from time 0 hours to infinity,
CL/F = clearance/bioavailability.

In a rat pharmacokinetic study, male Sprague Dawley rats are administered a single subcutaneous dose of 20 nmol/kg (0.084 mg/kg) of Compound II in Tris-mannitol buffer (pH 8.0) at a volume of 0.2 mL/kg. Blood is collected at 1-, 3-, 6-, 12-, 24-, 48-, 72-, 96-, 120-, and 144-hours post-dose for pharmacokinetic characterization. The results are shown in Table 7.

TABLE 7

Individual and Mean Plasma Pharmacokinetic Parameters Following a Single 20 nmol/kg Subcutaneous Dose of Compound II (SEQ ID NO: 2) to Male Sprague Dawley Rats

| Compound | Animal ID | $T_{1/2}$ (hr) | Tmax (hr) | Cmax (nmol/L) | $AUC_{0-inf}$ (hr * nmol/L) | CL/F (mL/hr/kg) |
|---|---|---|---|---|---|---|
| Compound II | R0001 | 47 | 48 | 88 | 8409 | 2.38 |
| | R0002 | 60 | 12 | 81 | 8702 | 2.30 |
| | R0003 | 67 | 12 | 99 | 8655 | 2.31 |
| | Mean | 58 | 24 | 90 | 8588 | 2.33 |
| | SD | 10 | 21 | 9 | 157 | 0.04 |

Abbreviations:
$T_{1/2}$ = half-life,
$T_{max}$ = time to maximum concentration,
$C_{max}$ = maximum observed plasma concentration,
$AUC_{0-inf}$ = area under the curve from time 0 hours to infinity,
CL/F = clearance/bioavailability.

The extended half-lives demonstrated by Compound II in Cynomolgus Monkeys show therapies with once weekly dose of Compound II is possible in patients.

EXAMPLE 6: IN VIVO EFFICACY IN DIET INDUCED OBESE (DIO) RATS OF COMPOUND II IN COMBINATION WITH OTHER INCRETIN COMPOUNDS

This study is conducted to investigate the effect of Compound II for diabetes and/or obesity conditions in DIO rats when administered in combination with other incretin compounds, including a GLP-1 agonist (Compound III), oxyntomodulin analog (Compound IV), and a triagonist of glucagon, GLP-1, and GIP (Compound V). Diet-induced obese (DIO) male Long Evans (Envigo) rats, maintained on a calorie rich diet since arrival at Lilly (TD95217; Teklad, Madison, Wis.), are used in the following studies. Animals are individually housed in a temperature-controlled (24° C.) facility with 12-hour light/dark cycle (lights on 2200) and free access to food (TD95217) and water.

The rats are randomized according to their body weight, so that each experimental group of animals would have similar body weight. The body weights range from 529 to 823 grams.

Each group contains five rats. Vehicle and Compound II (1 nmol/kg) are dissolved in vehicle (40 mM Tris-HCl pH8+0.02% PS80) and are administered by subcutaneous (SC) injection (1 mL/kg) to ad libitum fed DIO rats 30 to 90 minutes prior to the onset of the dark cycle every 3 days for 14 days. SC injections are made on Days 1, 4, 7, 10 and 13. Body weight and food intake are measured daily throughout the study. Absolute changes in body weight are calculated by subtracting the body weight of the same animal prior to the first injection of molecule.

At the end of the study, blood is collected to measure blood glucose and plasma insulin. Blood glucose is measured by AccuChek glucometers (Roche, Indianapolis, Ind.). Insulin is measured by ELISA (MSD, Rockville, Md.).

All data are presented as mean±SEM of 5 animals per group. Statistical analysis is performed using one-way ANOVA, followed by Tukey's multiple comparison test to compare treatment groups to vehicle group or each other. Significant differences are identified at $p<0.05$.

TABLE 8

The Effect of Compound II With and Without Combinations with Compound III, Compound IV, or Compound V on Body Weight and Cumulative Food Intake.

| Treatment* | Body Weight Change (g)** | Cumulative Food Intake (g)*** |
|---|---|---|
| Vehicle (10 mL/kg) | −3.42 ± 6.10 | 212.08 ± 16.84 |
| Compound II (1 nmol/kg) | −53.84 ± 2.85* | 137.38 ± 4.28* |
| Compound III (10 nmol/kg) | −54.20 ± 6.52* | 150.04 ± 5.71* |
| Compound IV (10 nmol/kg) | −50.24 ± 6.36* | 165.86 ± 7.45* |
| Compound V (3 nmol/kg) | −43.28 ± 2.54* | 157.50 ± 10.63* |
| Compound II + Compound III | −85.64 ± 5.08*#+ | 92.66 ± 11.52*#+ |
| Compound II + Compound IV | −85.43 ± 8.66*# | 113.58 ± 9.19*# |
| Compound II + Compound V | −89.70 ± 11.63*#+ | 97.16 ± 6.45*# |

*Treatments were subcutaneously administered every three days on Day 1, 4, 7, 10 and 13.
**Body weight measurements were made daily. Body weight change is the difference from Day-1 to Day 14 represented as grams.
***Cumulative food intake was the total food consumed throughout 14-day treatment period. Statistical analysis was done by one-way ANOVA followed by Tukey's.
*p < 0.05 compared to vehicle group;
p < 0.05 compared to either Compound III, Compound IV or Compound V group;
+p < 0.05 compared to Compound II.

EXAMPLE 7: AN ANALOGUE OF COMPOUND II IN COMBINATION WITH AN AGONIST OF GIP-GLP

This study is conducted to investigate the effect of an analog of Compound II for diabetes and/or obesity conditions in DIO rats when administered with Compound VI (SEQ ID NO:9), a dual agonist of GIP and GLP-1. Diet-induced obese (DIO) male Long Evans (Envigo) rats, maintained on a calorie rich diet since arrival at Lilly (TD95217; Teklad, Madison, Wis.), are used in the following studies. Animals are individually housed in a temperature-controlled (24° C.) facility with 12 hour light/dark cycle (lights on 2200) and free access to food (TD95217) and water.

The rats are randomized according to their body weight, so that each experimental group of animals would have similar body weight. The body weights range from 549 to 683 grams.

Each group contains five rats. Vehicle and Compound II (1 nmol/kg) dissolved in vehicle (10 mM Tris-HCl pH7.5, (50 mg/mL D-mannitol)+0.02% PS80) are administered by subcutaneous (SC) injection (1 mL/kg) to ad libitum fed DIO rats 30 to 90 minutes prior to the onset of the dark cycle every 3 days for 14 days. SC injections are made on Days 1, 4, 7, 10 and 13. Body weight and food intake are measured daily throughout the study. Absolute changes in body weight are calculated by subtracting the body weight of the same animal prior to the first injection of molecule.

At the end of the study, blood is collected to measure blood glucose and plasma insulin. Blood glucose is measured by AccuChek glucometers (Roche, Indianapolis, Ind.). Insulin is measured by ELISA (MSD, Rockville, Md.).

All data are presented as mean±SEM of 5 animals per group. Statistical analysis is performed using one-way ANOVA, followed by Tukey's multiple comparison test to compare treatment groups to vehicle group or each other. Significant differences are identified at $p<0.05$.

| Treatment* | Body Weight Change (g)** | Cumulative Food Intake (g)*** |
|---|---|---|
| Vehicle (10 ml/kg) | 6.18 ± 1.37 | 231.58 ± 1032 |
| Analog of Compound II (0.1 nmol/kg) | −24.82 ± 3.24* | 190.74 ± 6.56 |
| Compound VI (3 nmol/kg) | −18.10 ± 6.67* | 196.54 ± 16.98 |
| Analog of Compound II + Compound VI | −39.84 ± 2.20*# | 174 ± 6.48* |

*Treatments were subcutaneously administered every three days on Day 1, 4, 7, 10 and 13.
**Body weight measurements were made daily. Body weight change is the difference from Day-1 to Day 16 represented as grams.
***Cumulative food intake was the total food consumed throughout 16-day treatment period. Statistical analysis was done by one-way ANOVA followed by Tukey's.
*p < 0.05 compared to vehicle group;
p < 0.05 compared to GIP-706.

An analogue of Compound II in combination with Compound VI caused more weight loss than individual treatment which is likely mainly attributable to significant decrease in cumulative food intake induced by combination treatment.

EXAMPLE 8: IMMUNOGENICITY RISK ASSESSMENT

MAPPs Assay (MHC-Associated Peptide Proteomics):

Primary human dendritic cells from ten normal human donors are prepared from buffy coats by isolation of CD14+ cells and differentiated into immature dendritic cells by incubation with 20 ng/mL IL-4 and 40 ng/mL GM-CSF in complete RPMI media containing 5% Serum Replacement (Thermo Fisher Scientific, cat #A2596101) for three days at 37° C. and 5% $CO_2$ as described (Knierman et al., "The Human Leukocyte Antigen Class II Immunopeptidome of the SARS-CoV-2 Spike Glycoprotein", Cell Reports, 33, 108454 (2020)). Three micromolar of test antibody is added to approximately $5 \times 10^6$ cells on day 4 and fresh media containing 5 µg/mL of LPS to transform the cells into mature dendritic cells is exchanged after 5-hour incubation. The matured cells are lysed in 1 mL of RIPA buffer with protease inhibitors and DNAse the following day. The lysates are stored at −80° C. until sample analysis.

An automated liquid handling system is used to isolate the HLA-II molecules from thawed lysate using biotinylated anti-pan HLA class II antibody (clone Tu39). The bound receptor-peptide complex is eluted with 5% acetic acid, 0.1% TFA. The eluted MHC-II peptides are passed over a prewashed 10k MWCO filter to remove high molecular weight proteins. The isolated MHC-II peptides are analyzed by nano LC/MS using a Thermo easy 1200 nLC-HPLC system with a Thermo LUMOS mass spectrometer. The separation used a 75 µm×7 cm YMC-ODS $C_{18}$ column for 65-minute gradient with a 250 nL/min flow rate and 0.1% formic acid in water as A solvent and 80% acetonitrile with 0.1% formic acid as B solvent. Mass spectrometry is run in full scan mode with 240,000 resolution followed by a 3 second data dependent MS/MS cycle comprised of ion trap rapid scans with HCD and EThcD fragmentation.

Peptide identifications are generated by an internal proteomics pipeline (Higgs et al., "Label-free LC-MS method for the identification of biomarkers", Methods in Molecular Biology, 428, 209-230 (2008)) using multiple search algorithms with no enzyme search parameter against a bovine/human database containing the test antibody sequences. A KNIME workflow is used to process the identification files for the samples. Peptides identified from the test articles are aligned against the parent sequence. A summary is created for all donors that annotates the percent of donors that display non-germline residues, the number of different regions that display peptides with non-germline residues and the depth of peptide display at each region with non-germline residues. Increases in the extent of display of non-germline peptides is associated with increased risk for immunogenicity. Results for Compound II are shown in Table 9 and suggest a low level of immunogenicity risk associated with Compound II.

TABLE 9

MAPPs Results

| Test Compound | % Donors | # of clusters | Total # of non-germline residues from all clusters | Total # of non-germline peptides from all clusters |
|---|---|---|---|---|
| Compound II | 0% | 0 | n/a* | n/a* |

*n/a designates totals are not applicable because there were no donors displaying non-germline residues.

T Cell Proliferation Assay

This assay assesses the ability of test candidate to activate CD4+ T cells by inducing cellular proliferation as described (Walsh et al., "Post-hoc assessment of the immunogenicity of three antibodies reveals distinct immune stimulatory mechanisms", mAbs, 12, 1764829 (2020)). Cryopreserved PBMCs were used from ten healthy donors and the CD8+ T cells were depleted from the PBMCs and labeled with 1 Carboxyfluorescein Diacetate Succinimidyl Ester (CFSE). PBMCs were seeded at $4 \times 10^6$ cells/ml/well in AIM-V media (Life Technologies, cat #12055-083) containing 5% CTS™ Immune Cell SR (Gibco, cat #A2596101) and tested in triplicate in 2.0 mL containing the different test articles, media control, keyhole limpet haemocyanin (KLH; positive control), lixisenatide (assay positive control), or Compound II. Cells were cultured and incubated for 7 days at 37° C. with 5% $CO_2$. On day 7, samples were stained with the following cell surface markers: anti-CD3, anti-CD4, anti-CD14, anti-CD19, and DAPI for viability detection by flow cytometry using a BD LSRFortessa™, equipped with a High Throughput Sampler (HTS). Data was analyzed using FlowJo® Software (FlowJo, LLC, TreeStar) and a Cellular Division Index (CDI) was calculated. Briefly, the CDI for each test candidate's MAPPs-derived peptide cluster was calculated by dividing the percent of proliferating $CFSE^{dim}CD4+$ T cells from peptide-stimulated wells by the percent of proliferating $CFSE^{dim}CD4+$ T cells in the unstimulated wells. A CDI of >2.5 was considered to represent a positive response. A percent donor frequency across all donors was evaluated. All donors produced a positive T cell response against KLH (100%). The clinical immunogenic positive control lixisenatide induced a positive T cell response of 50% of the cohort in this study. This falls within the expected range for this assay (40-90% Positive Donor Frequency). Results for Compound II are shown in Table 10 and suggest a low level of immunogenicity risk for Compound II.

TABLE 10

The Frequency of CD4+ T cell Responses

| Molecule Tested | % Positive Donors | Median CDI (Positive Donors) | Median CDI (All donors) | Range High | Range Low | Number of donors |
|---|---|---|---|---|---|---|
| KLH | 100.0 | 36.2 | 36.2 | 171.4 | 4.5 | 8/8 |
| Lixisenatide | 50 | 3.0 | 2.5 | 5.7 | 1.2 | 4/8 |
| Compound II | 12.5 | 19.7 | 1.0 | 19.7 | 0.7 | 1/8 |

Sequences

Compound I (SEQ ID NO:1)
Acetyl-ASHLSTAVLGKLS-Aib-ELHKLEDYPRTDV-GAESP-$NH_2$
Compound II (SEQ ID NO:2)
Acetyl-ASHLSTAVLGK((2-[2-(2-Amino-ethoxy)-ethoxy]-acetyl)$_2$-($\gamma$-Glu)-CO—$(CH_2)_{18}$—$CO_2$H)LS-Aib-ELHKLE-DYPRTDVGAESP-$NH_2$
Pramlintide (SEQ ID NO:3)
KCNTATCATQRLANFLVHSSNNFGPILPPTNVGSNTY-$NH_2$ with a disulfide bond between Cys 2 and Cys 7
Human calcitonin (SEQ ID NO:4)
CGNLSTCMLGTYTQDFNKFHTFPQTAIGVGAP-$NH_2$ with a disulfide bond between Cys 1 and Cys 7
Human amylin (SEQ ID NO:5)
KCNTATCATQRLANFLVHSSNNFGAILSSTNVGSNTY-$NH_2$ with a disulfide bond between Cys 2 and Cys 7
Compound III (SEQ ID NO:6)
H-Aib-EGTFTSDVSSYLEGQAAK((2-[2-(2-Amino-ethoxy)-ethoxy]-acetyl)$_2$-($\gamma$Glu)-CO—$(CH_2)_{16}$—$CO_2$H) EFIAWLVRGRG
Compound IV (SEQ ID NO:7)
H-Aib-QGTFTSDYSKYLDEKKAK((2-[2-(2-Amino-ethoxy)-ethoxy]-acetyl)$_2$-($\gamma$Glu)-CO—$(CH_2)_{18}$—$CO_2$H) EFVEWLLEGGPSSG-$NH_2$
Compound V (SEQ ID NO:8)
Y-Aib-QGTFTSDYSI-$\alpha$MeL-LDKK((2-[2-(2-Amino-ethoxy)-ethoxy]-acetyl)-($\gamma$Glu)-CO—$(CH_2)_{18}$—$CO_2$H)AQ-Aib-AFIEYLLEGGPSSGAPPPS-$NH_2$
Compound VI (SEQ ID NO:9)
Y-Aib-EGTFTSDYSI-Aib-LDKIAQK((2-[2-(2-Amino-ethoxy)-ethoxy]-acetyl)$_2$-($\gamma$Glu)$_2$-CO—$(CH_2)_{18}$—$CO_2$H) A-(1Nal)-VQWLIAGGPSSGAPPPS-$NH_2$
Compound VII (SEQ ID NO:10)
YX$_1$EGTFTSDYSIX$_2$LDKIAQKAFVQWLIAGGPSSGA-PPPS wherein $X_1$ is Aib; $X_2$ is Aib; K at position 20 is chemically modified through conjugation to the epsilon-amino group of the K side-chain with (2-[2-(2-Amino-ethoxy)-ethoxy]-acetyl)$_2$-($\gamma$Glu)$_1$-CO—$(CH_2)_{18}$—$CO_2$H; and the C-terminal amino acid is amidated as a C-terminal primary amide.

CAS Registry Number: 2023788-19-2
Lixisenatide (SEQ ID NO:11) HGEGTFTSDLSKQMEEE-
AVRLFIEWLKNGGPSSGAPPSKKKKKK-NH$_2$ CAS
Registry Number: 320367-13-3
Compound VIII (SEQ ID NO:12)
HAEGTFTSDVSSYLEGQAAK(γGlu-CO—(CH$_2$)$_{14}$—
CH$_3$)EFIAWLVRGRG CAS Registry Number: 204656-
20-2
Compound IX (SEQ ID NO:13)

Dulaglutide is a human GLP-1 receptor agonist which comprises a dimer of a GLP-1 analog fused at its C-terminus via a peptide linker to the N-terminus of an analog of an Fc portion of an immunoglobulin, and is identified by CAS registry number 923950-08-7, which provides the following chemical name: 7-37-Glucagon-like peptide I [8-glycine, 22-glutamic acid, 36-glycine] (synthetic human) fusion protein with peptide (synthetic 16-amino acid linker) fusion protein with immunoglobulin G4 (synthetic human Fc fragment), dimer. Each monomer of dulaglutide has the amino acid sequence set forth in SEQ ID NO:13:

HGEGTFTSDVSSYLEEQAAKEFIAWLVKGGGGGGGSGGGGSGGG

GSAESKYGPPCPPCPAPEAAGGPSVFLFPPKPKDTLMISRTPEV

TCVVVDVSQEDPEVQFNWYVDGVEVHNAKTKPREEQFNSTYRVV

SVLTVLHQDWLNGKEYKCKVSNKGLPSSIEKTISKAKGQPREPQ

VYTLPPSQEEMTKNQVSLTCLVKGEYPSDIAVEWESNGQPENNY

KTTPPVLDSDGSFFLYSRLTVDKSRWQEGNVFSCSVMHEALHNH

YTQKSLSLSLG

We claim:

1. A compound comprising: Acetyl-ASHLSTAVLGK((2-[2-(2-Amino-ethoxy)-ethoxy]-acetyl)$_2$-(γ-Glu)-CO—(CH$_2$)$_{18}$—CO$_2$H)LS-Aib-ELHKLEDYPRTDVGAESP-NH$_2$ (SEQ ID NO:2), or a pharmaceutically acceptable salt thereof.

2. A method of treating Type 2 diabetes in a patient in need thereof, comprising administering to the patient an effective amount of a compound of claim 1, or a pharmaceutically acceptable salt thereof.

3. A method of treating obesity in a patient in need thereof, comprising administering to the patient an effective amount of a compound of claim 1, or a pharmaceutically acceptable salt thereof.

4. A method of treating dyslipidemia in a patient in need thereof, comprising administering to the patient an effective amount of a compound of claim 1, or a pharmaceutically acceptable salt thereof.

5. A method of treating non-alcoholic steatohepatitis (NASH) in a patient in need thereof, comprising administering to the patient an effective amount of a compound of claim 1, or a pharmaceutically acceptable salt thereof.

6. A method of lowering food intake in a patient in need thereof, comprising administering to the patient an effective amount of a compound of claim 1, or a pharmaceutically acceptable salt thereof.

7. A method of lowering body weight in a patient in need thereof, comprising administering to the patient an effective amount of a compound of claim 1, or a pharmaceutically acceptable salt thereof.

8. A method of lowering blood glucose in a patient in need thereof, comprising administering to the patient an effective amount of a compound of claim 1, or a pharmaceutically acceptable salt thereof.

9. A method of lowering triglycerides in a patient in need thereof, comprising administering to the patient an effective amount of a compound of claim 1, or a pharmaceutically acceptable salt thereof.

10. A pharmaceutical composition comprising the compound of claim 1, or a pharmaceutically acceptable salt thereof, and at least one pharmaceutically acceptable excipient.

11. A method of treating a condition in a patient in need thereof, selected from the group consisting of: clinical or pre-clinical diabetes, obesity, NASH, and dyslipidemia, comprising administering to the patient an effective amount of the pharmaceutical composition of claim 10.

12. A method of treating a condition in a patient in need thereof, selected from the group consisting of: clinical or pre-clinical diabetes, obesity, NASH, and dyslipidemia, comprising administering to the patient an effective amount of the pharmaceutical composition of claim 10 in combination with an effective amount of an incretin or incretin analog.

13. A compound consisting of: Acetyl-ASHLSTAVLGK((2-[2-(2-Amino-ethoxy)-ethoxy]-acetyl)$_2$-(γ-Glu)-CO—(CH$_2$)$_{18}$—CO$_2$H)LS-Aib-ELHKLEDYPRTDVGAESP-NH$_2$ (SEQ ID NO:2), or a pharmaceutically acceptable salt thereof.

\* \* \* \* \*